US00RE42715E

(19) United States
(12) Reissued Patent
Sones

(10) Patent Number: US RE42,715 E
(45) Date of Reissued Patent: Sep. 20, 2011

(54) VISION SYSTEM AND METHOD FOR PROCESS MONITORING

(75) Inventor: Richard A. Sones, Cleveland, OH (US)

(73) Assignee: Applied Vision Corporation, Cuyahoga Falls, OH (US)

(21) Appl. No.: 12/775,597

(22) Filed: May 7, 2010

Related U.S. Patent Documents

Reissue of:
(64) Patent No.: 7,394,937
Issued: Jul. 1, 2008
Appl. No.: 10/849,955
Filed: May 19, 2004

(51) Int. Cl.
*G06K 9/68* (2006.01)
*G06K 9/00* (2006.01)
*G06K 9/62* (2006.01)

(52) U.S. Cl. ..... 382/218; 382/141; 382/159

(58) Field of Classification Search ..... 382/103, 382/141–149, 159, 165, 209, 216, 218, 219; 348/92, 169, 237
See application file for complete search history.

(56) References Cited

U.S. PATENT DOCUMENTS 5,245,399 A 9/1993 Wertz et al.
5,544,240 A 8/1996 Warren
5,754,448 A 5/1998 Edge et al.
5,818,443 A 10/1998 Schott
5,835,244 A 11/1998 Bestmann
5,911,003 A 6/1999 Sones
6,134,343 A * 10/2000 Nichani ..... 382/141
6,249,600 B1 6/2001 Reed et al.
6,340,976 B1 1/2002 Oguchi et al.
6,459,425 B1 10/2002 Holub et al.
6,501,850 B2 12/2002 Setchell, Jr.
6,701,001 B1 3/2004 Kenneway et al.
7,187,472 B2 3/2007 Friedman et al.
2003/0179920 A1 9/2003 Hooker et al.
2004/0247193 A1 * 12/2004 Qualtrough et al. ..... 382/243

OTHER PUBLICATIONS

Hardeberg, et al., "Multispectral image capture using a tunable filter," Ecole Nationale Superieure des Telecommunications (Paris, France).

* cited by examiner

*Primary Examiner* — Daniel Mariam
(74) *Attorney, Agent, or Firm* — Hahn Loeser & Parks LLP

(57) ABSTRACT

A method and system to monitor randomly oriented objects on a process line are disclosed. A color camera is used initially to collect a set of reference images of at least one reference object. The reference images represent various spatial orientations of the reference object. The reference object serves as the standard for the process. The reference images are stored in a computer-based platform. The color camera is then used to capture images of monitored objects as the monitored objects pass by the color camera on a process line. The monitored objects may have a random spatial orientation with respect to the color camera as the monitored objects pass through the field-of-view of the color camera. The captured images of the monitored objects are processed by the computer-based platform and compared to the reference images in order to determine if certain characteristic parameters of the monitored objects have deviated from those same characteristic parameters of the reference object. If so, the process may be adjusted to correct for the deviations in order to bring the process back into tolerance.

41 Claims, 14 Drawing Sheets

VISION SYSTEM AND METHOD FOR PROCESS MONITORING

Matter enclosed in heavy brackets [ ] appears in the original patent but forms no part of this reissue specification; matter printed in italics indicates the additions made by reissue.

CROSS-REFERENCE TO RELATED APPLICATIONS/INCORPORATION BY REFERENCE

U.S. patent application Ser. No. 10/404,027, filed on Apr. 1, 2003, is incorporated herein by reference in its entirety. Also, U.S. patent application Ser. No. 10/411,741, filed on Apr. 10, 2003, is incorporated herein by reference in its entirety.

TECHNICAL FIELD

Certain embodiments of the present invention relate to process monitoring and correction. More particularly, certain embodiments of the present invention relate to a vision system and method for monitoring a process in order to control certain characteristic parameters of monitored objects such as, for example, absolute color.

BACKGROUND OF THE INVENTION

Manufacturers of products that are produced in high volume as part of a process using, for example, a process line, employ quality assurance methods to ensure that certain features of the product (e.g., color, pattern, alignment, texture) are consistent and match a production reference standard. For example, in the soda can industry, the patterns and colors on the outer surface of the cans should be monitored somehow as the cans proceed down a process line to ensure that the process of printing the outer surface of the cans does not result in out of tolerance conditions (e.g., color drift, pattern alignment drift, etc.). The product moving down a process line is often spatially oriented in a random manner along the process line. For example, soda cans having a specific pattern printed on the cylindrical outer surface are typically oriented randomly about the vertical axis of rotation of the predominantly cylindrical can.

These methods can be as simple as a production floor operator performing a set-up of a product run by making visual comparison of a finished set-up part to a standard reference chart or reference part. Based on this comparison the operator makes adjustments to the process. Then another set-up part is created and compared, more adjustments made until acceptable results are achieved, and the product run is initiated. This subjective method may lead to errors because of differences in the ambient light conditions, positions of the inspection light source, and differences in surface textures between the reference part and the finished part, different people conducting the comparisons, and other factors. While such a subjective comparison may be appropriate for some manufacturing processes, other more sophisticated processes (e.g., multi-color processes) may require more objective techniques.

Examples of such processes include package printing processes, soda can printing processes, and other processes which may employ more complex color schemes that are repeated or are placed next to each other in use. Besides merely color concerns, these complex color schemes may have spatial or pattern defects. A trained quality assurance color inspector using a standard illuminant may be able to catch many of these defects by using a subjective comparison with a standard reference part, however, many of such defects may not be discernible to the naked eye. In such applications, manufacturers have typically used a color densitometer, a tristimulus calorimeter, or a reflectance spectrophotometer to provide more precise color matching by utilizing colorimetry, discussed in more detail below.

The process of quantitative color analysis is generally referred to as colorimetry. Since the introduction of the CIE (Commission International de l'Eclairage) color measurement system in the early 1930's, many different measurement systems have been proposed for different applications. One such measurement system is the CIE XYZ color space. The CIE XYZ color space characterizes colors by a luminance parameter Y and two color coordinates X and Z which specify the point on the chromaticity diagram. The XYZ parameters are based on the spectral power distribution of the light emitted from a colored object and are factored by sensitivity curves which have been measured for the human eye. The human eye has three different types of color-sensitive cones. Accordingly, the XYZ functions were intended to correspond to the average sensitivity of the human eye and provide a device-independent representation of color. Therefore, the spectral responses of the XYZ functions are known as "tristimulus" functions and make up the coordinate system to quantify a color image or color space.

The apparent color of an object depends not only on its intrinsic spectral reflectivity, but also on the spectrum of the light used to illuminate it. The CIE also has defined a number of standard illuminants which are defined, theoretically, in terms of their spectral content. To completely specify the color of an object, one must measure the XYZ values of the light emanating from the object when it is illuminated by a standard illuminant.

Another CIE color space which is frequently used is the L*a*b* color space. The values of L*, a*, and b* are derived mathematically from the tristimulus values of X, Y, and Z:

$$L^* = 116\left(\frac{Y}{Y_n}\right)^{1/3} - 16$$

$$a^* = 500\left[\left(\frac{X}{X_n}\right)^{1/3} - \left(\frac{Y}{Y_n}\right)^{1/3}\right]$$

$$b^* = 200\left[\left(\frac{Y}{Y_n}\right)^{1/3} - \left(\frac{Z}{Z_n}\right)^{1/3}\right]$$

where the values with the subscript "n" are found in published tables and correspond to a chosen standard illuminant. The value of L* is proportional to the brightness (luminosity) of the color. The value of a* describes the red/green composition of the color. The value of b* describes the yellow/blue composition of the color.

The goal of the L*a*b* color space is to provide a color space where the Euclidean distance between color 1 and color 2

$$\Delta E = \sqrt{(\Delta L^*)^2 + (\Delta a^*)^2 + (\Delta b^*)^2}$$

wherein:

$$\Delta L^* = L_1^* - L_2^*$$

$$\Delta a^* = a_1^* - a_2^*$$

$$\Delta b^* = b_1^* - b_2^*$$

is a "perceptually uniform" measure of the difference between color 1 and color 2. A value of $\Delta E=1$ corresponds to a color difference which is very subtle—so subtle that it would take a trained color observer working under ideal lighting conditions to notice the difference. A value of ΔE=2 corresponds to a difference in color which is twice as noticeable as ΔE=1, and so on. The "perceptual distance" denoted by a given value of ΔE is intended to be independent of the location in color space (that is, independent of hue, saturation, and brightness), but this independence is actually only an approximation. Regardless, ΔE has been accepted in the color industry to quantify color differences.

As stated above, manufacturers typically have used a tristimulus colorimeter, a reflectance spectrophotometer, or a color densitometer to provide more precise color matching by utilizing one or more color measurement systems. These instruments provide quantitative and objective feedback, but are slow and inconvenient, and only measure color at one small spot (typically 5 mm in diameter) at a time, making it inconvenient to impossible to use them to compare all the colors on a complex multi-color pattern. In addition, these devices tend to be expensive due to the manufacturing care necessary to construct a device capable of providing precise color measurements suitable for laboratory use. These disadvantages make these devices particularly unsuitable for the production floor for use in process control.

Another disadvantage with densitometers is that they do not provide absolute color metrics (such as XYZ tristimulous values). Instead, they report the overall reflectivity of a surface for red, green, and blue light. Color densitometers are only suited for relative (as opposed to absolute) measurements. These relative measurements are often sufficient when the goal is simply to determine if the color on one object "matches" the color on another object.

Therefore there remains a need in the art for a fast and convenient way to efficiently monitor a production process with respect to a standard reference, where the production objects being monitored may have a random spatial orientation, at least around one axis.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises a method for monitoring a process. The method includes generating a set of reference images of at least one reference object using a vision training system. Each reference image of the set of reference images corresponds to a unique and precise spatial orientation of the reference object with respect to the training system. The method further includes acquiring one monitored image from each of a plurality of randomly oriented monitored objects over a period of time using a process monitoring system. Each of the plurality of monitored objects is substantially identical to the reference object. However, there may be differences from the reference object due to process variations. The method also includes comparing at least one acquired monitored image of the plurality of monitored objects to the set of reference images of the reference object to form at least one comparison image of comparison values. The method further includes generating at least one process deviation value in response to the comparing step.

Another embodiment of the present invention comprises a vision training system for characterizing a reference object. The training system includes a rotatable staging platform to stage a reference object and a source of illumination to illuminate the reference object on the staging platform. The training system further includes a color camera to collect a set of reference images of the reference object as the reference object rotates on the rotatable staging platform. Each reference image of the set of reference images corresponds to a unique and precise rotational position of the reference object with respect to the color camera. The training system also includes a computer-based platform connected to the color camera to store and process the set of reference images.

A further embodiment of the present invention comprises a vision monitoring system for monitoring a process. The monitoring system includes a source of illumination positioned to illuminate objects to be monitored as the objects move along a process line. The monitoring system further includes a color camera positioned on the process line to capture at least one image from each illuminated object, forming a plurality of monitored images, as each illuminated object passes through a field-of-view of the color camera. The monitoring system also includes a computer-based platform storing a set of reference images and being connected to the color camera to store the plurality of monitored images and to generate at least one process deviation value by comparing at least one monitored image of the plurality of monitored images to the set of reference images.

These and other advantages and novel features of the present invention, as well as details of an illustrated embodiment thereof, will be more fully understood from the following description and drawings.

DETAILED DESCRIPTION OF THE INVENTION

Figure 1:
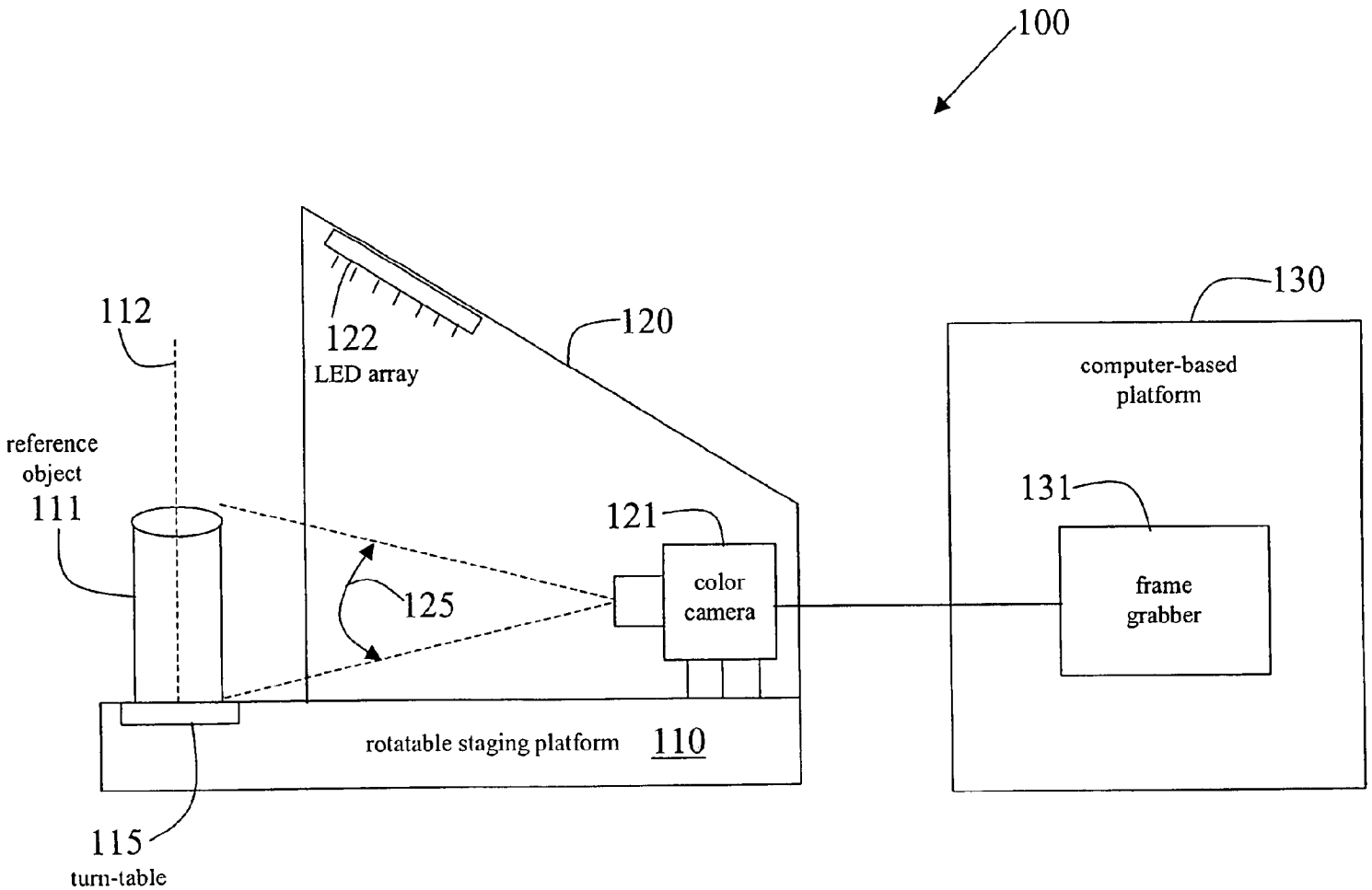
FIG. 1 illustrates an embodiment of a vision training system for collecting images from reference objects, in accordance with various aspects of the present invention.

FIG. 1 illustrates an embodiment of a vision training system 100 for collecting images from reference objects, in accordance with various aspects of the present invention. The training system 100 includes a rotatable staging platform 110 which is used to stage a reference object 111 to be imaged. The rotatable staging platform 110 includes a turn-table 115 which is used to rotate the reference object 111 about an axis of rotation 112. The reference object 111 represents a "gold standard" production part which is desired to be replicated many times with respect to certain characteristic features. Several reference objects may actually be used for training.

The training system 100 also comprises an imaging assembly 120 which includes a color camera 121 and a source of illumination 122. The imaging assembly 120 is attachable to the rotatable staging platform 110 such that, as the reference object 111 rotates, the reference object 111 is within the field of view 125 of the color camera 121 and is illuminated by the source of illumination 122. In accordance with an embodiment of the present invention, the source of illumination 122 comprises an array of light emitting diodes (LEDs) having a white light spectrum. Such a white light spectrum is useful for determining the true colors of the reference object.

The training system 100 also includes a computer based-platform 130 connected to the color camera 121 in order to store and process image data of the reference object 111 collected by the color camera 121. In accordance with an embodiment of the present invention, the computer-based platform 130 comprises a standard, commercial, off-the-shelf personal computer running a general purpose operating system. However, the computer-based platform 130 also includes image processing software tools which may be commercially available and/or customized software. In accordance with an embodiment of the present invention, the computer-based platform 130 also provides control signals to the color camera 121 in order to control certain functionality of the color camera 121 (e.g., image capture rate).

In accordance with an embodiment of the present invention, the color camera 121 outputs analog imaging signals and the computer-based platform 130 includes a frame grabber 131 to convert the analog imaging signals to frames of digital imaging data. In accordance with another embodiment of the present invention, the color camera 121 outputs digital imaging signals and the frame grabber 131 is not used. The color camera 121 comprises a three-color camera providing RGB (red, green, blue) color imaging signals. Examples of three-color cameras include: CCD video cameras—still cameras, CID video cameras—still cameras, etc. In accordance with an alternative embodiment of the present invention, the camera 121 comprises a gray scale or monochrome camera.

In use, the training system 100 captures color images of the reference object 111 (e.g., a largely cylindrical can with printed graphics and text on its outer surface) as the reference object 111 rotates on the turn-table 115. The reference object 111 represents an ideal standard of the objects to be monitored on a production process line.

In accordance with one embodiment of the present invention, sixteen reference images are collected from the reference object using the color camera 121 such that each of the sixteen reference images correspond to one unique, precise vertical segment or strip of the outer surface of the reference object 111. That is, each of the sixteen reference images correspond to a unique rotational position of the reference object 111 with respect to the field-of-view 125 of the color camera 121 as the reference object 111 is rotated about the axis 112. The sixteen images cover all 360 degrees about the circumference of the reference object 111. These reference images are transferred and digitally stored in the computer-based platform 130 as arrays of pixel data (e.g., RGB color values).

In accordance with an embodiment of the present invention, the reference images are processed by the computer-based platform 130 to correct for lighting non-uniformity due to variations in the source of illumination 122 and/or due to the spatial relationship between the source of illumination 122, the reference object 111, and the color camera 121. A white reference image may initially be used with a brightness reference strip to calibrate the training system 100 such that reference images of true reference objects (e.g., soda cans) can be subsequently corrected for lighting non-uniformity. The reference images will subsequently be used in a process monitoring system to compare monitored images from monitored objects on a processing line to the reference images in order to ensure process control.

Figure 2:
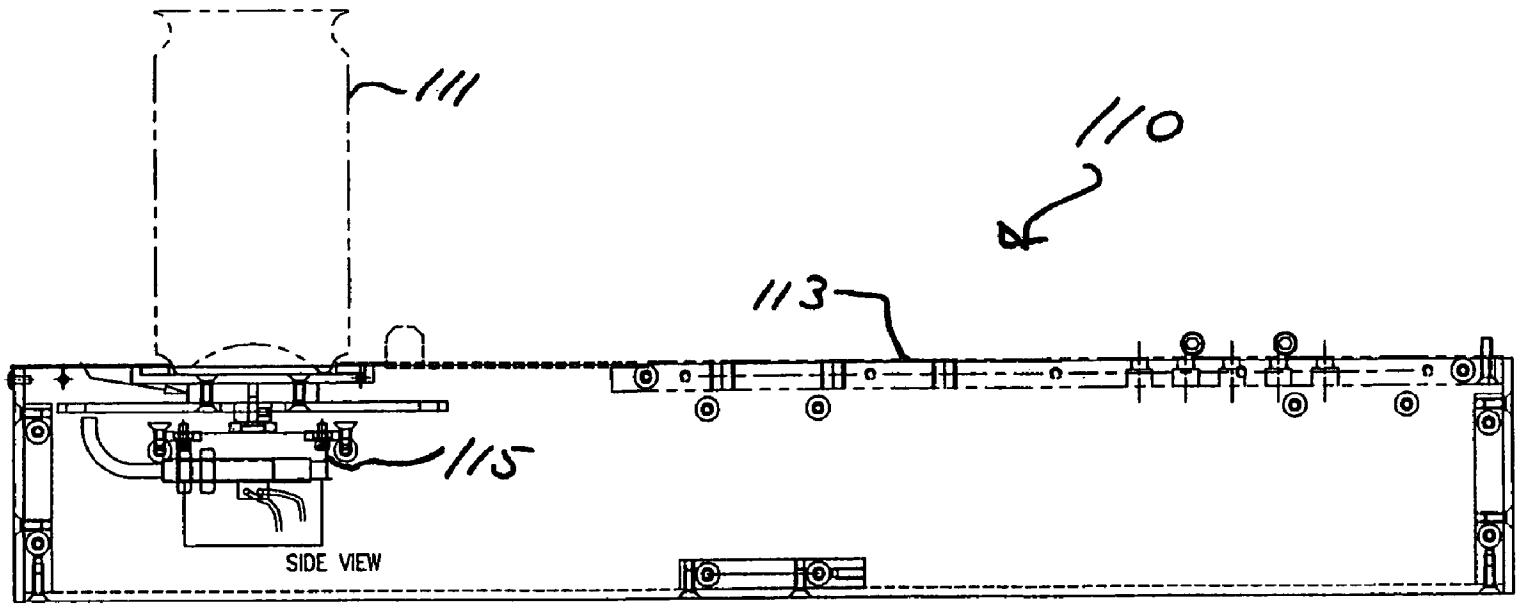
FIG. 2 illustrates an embodiment of a rotatable staging platform used in the training system of FIG. 1, in accordance with various aspects of the present invention.

FIG. 2 illustrates an embodiment of a rotatable staging platform 110 used in the training system 100 of FIG. 1, in accordance with various aspects of the present invention. The rotatable staging platform 110 includes a mounting surface 113 to allow attachment of the imaging assembly 120. Certain details of the turn-table 115 are also shown.

Figure 3:
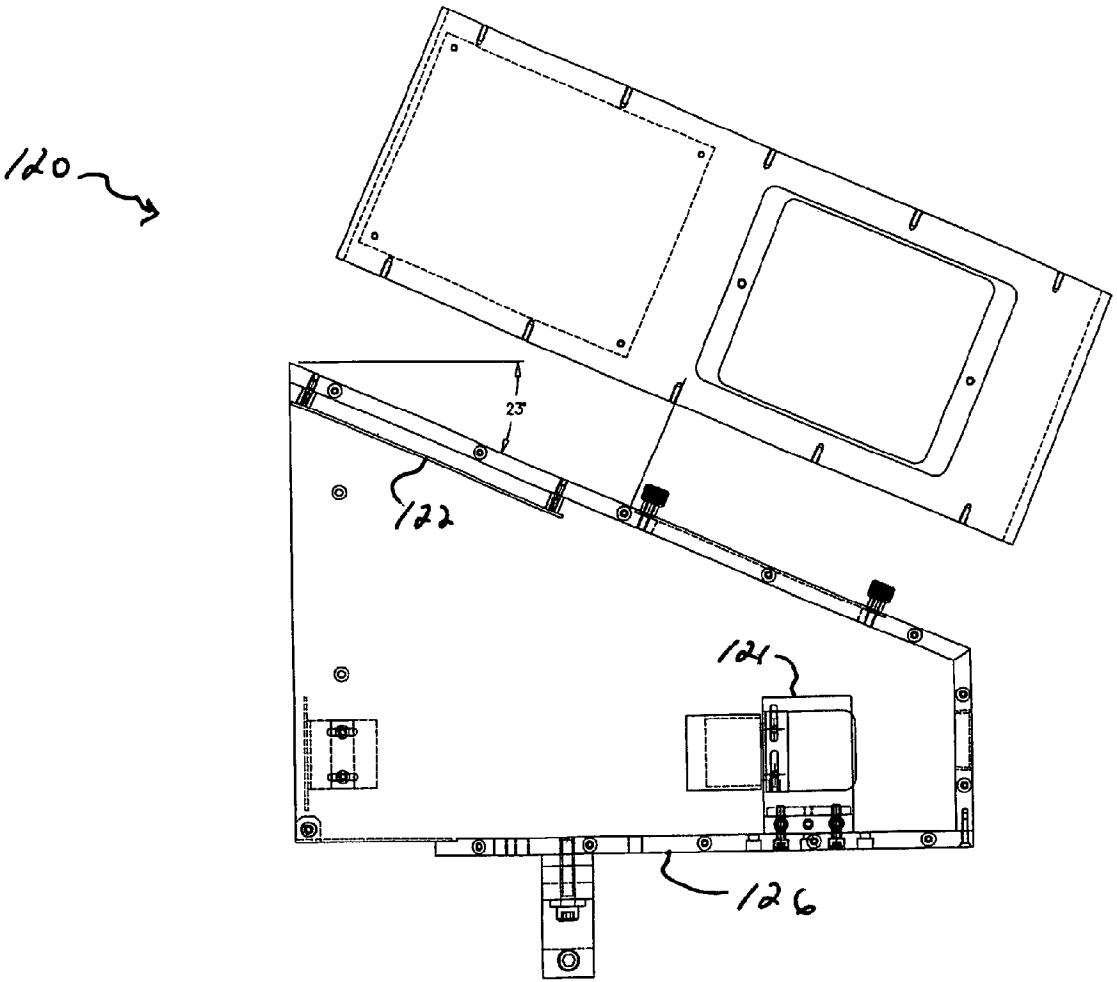
FIG. 3 illustrates an embodiment of an imaging assembly used in the training system of FIG. 1, in accordance with various aspects of the present invention.
Figure 4:
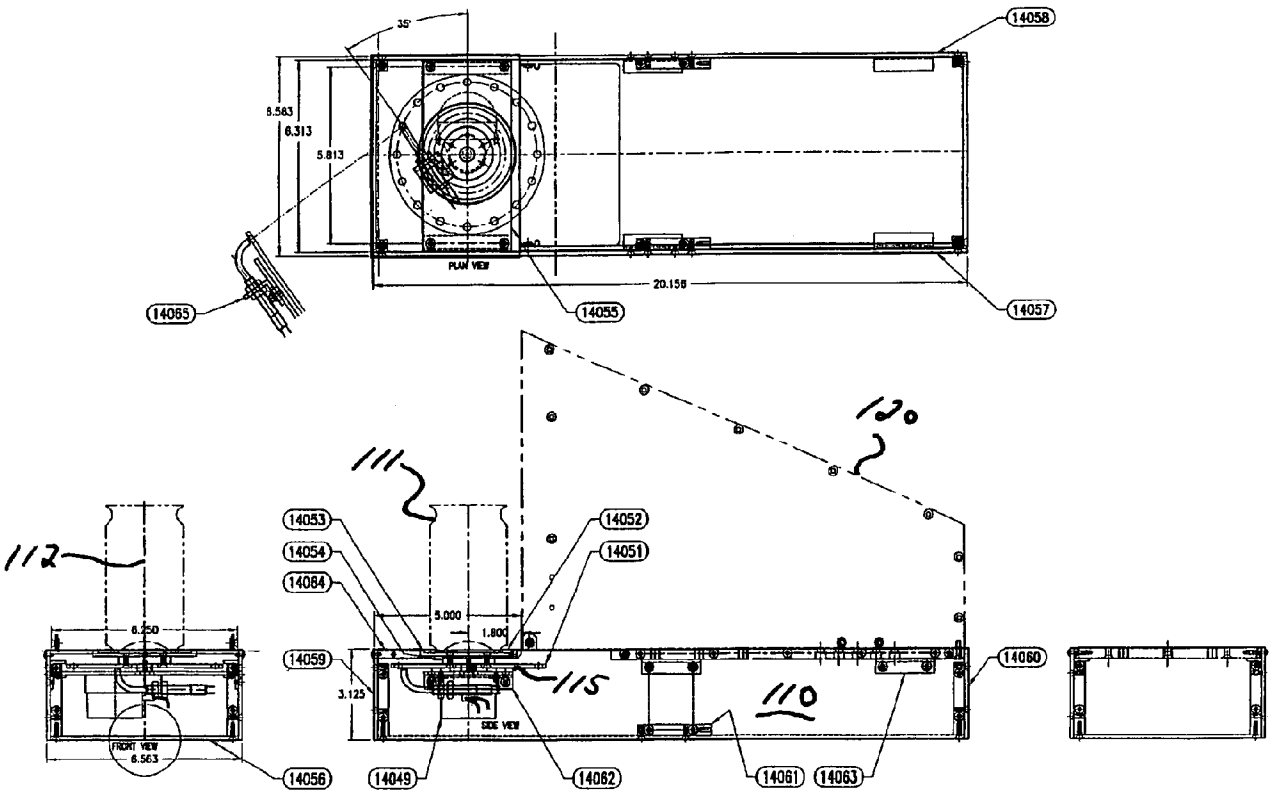
FIG. 4 illustrates several views of the rotatable staging platform of FIG. 2 and how it attaches to the imaging assembly of FIG. 3, in accordance with an embodiment of the present invention.
Figure 5:
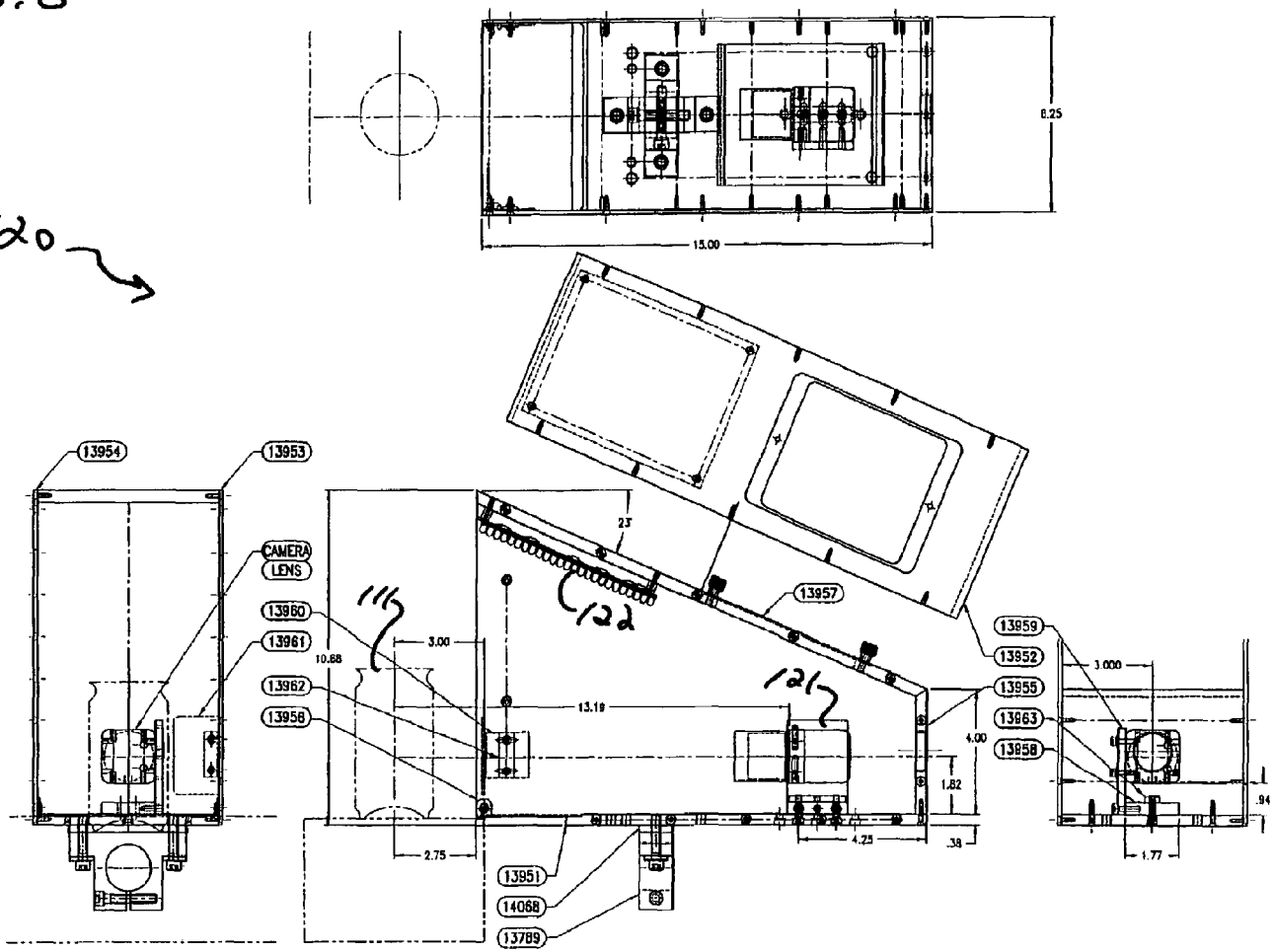
FIG. 5 illustrates several views of the imaging assembly of FIG. 3, in accordance with an embodiment of the present invention.

FIG. 3 illustrates an embodiment of an imaging assembly 120 used in the training system 100 of FIG. 1, in accordance with various aspects of the present invention. The imaging assembly 120 includes a mounting surface 126 to allow attachment to the rotatable staging platform 110. FIG. 4 illustrates several views of the rotatable staging platform 110 of FIG. 2 and how it attaches to the imaging assembly 120 of FIG. 3, in accordance with an embodiment of the present invention. FIG. 5 illustrates several views of the imaging assembly 120 of FIG. 3, in accordance with an embodiment of the present invention.

The training system 100 may also include a user interface including a display which may be used by an operator to view images and to control the training system 100 via, for example, a menu-driven touch-screen display. The user interface connects to the computer-based platform 130.

Figure 6:
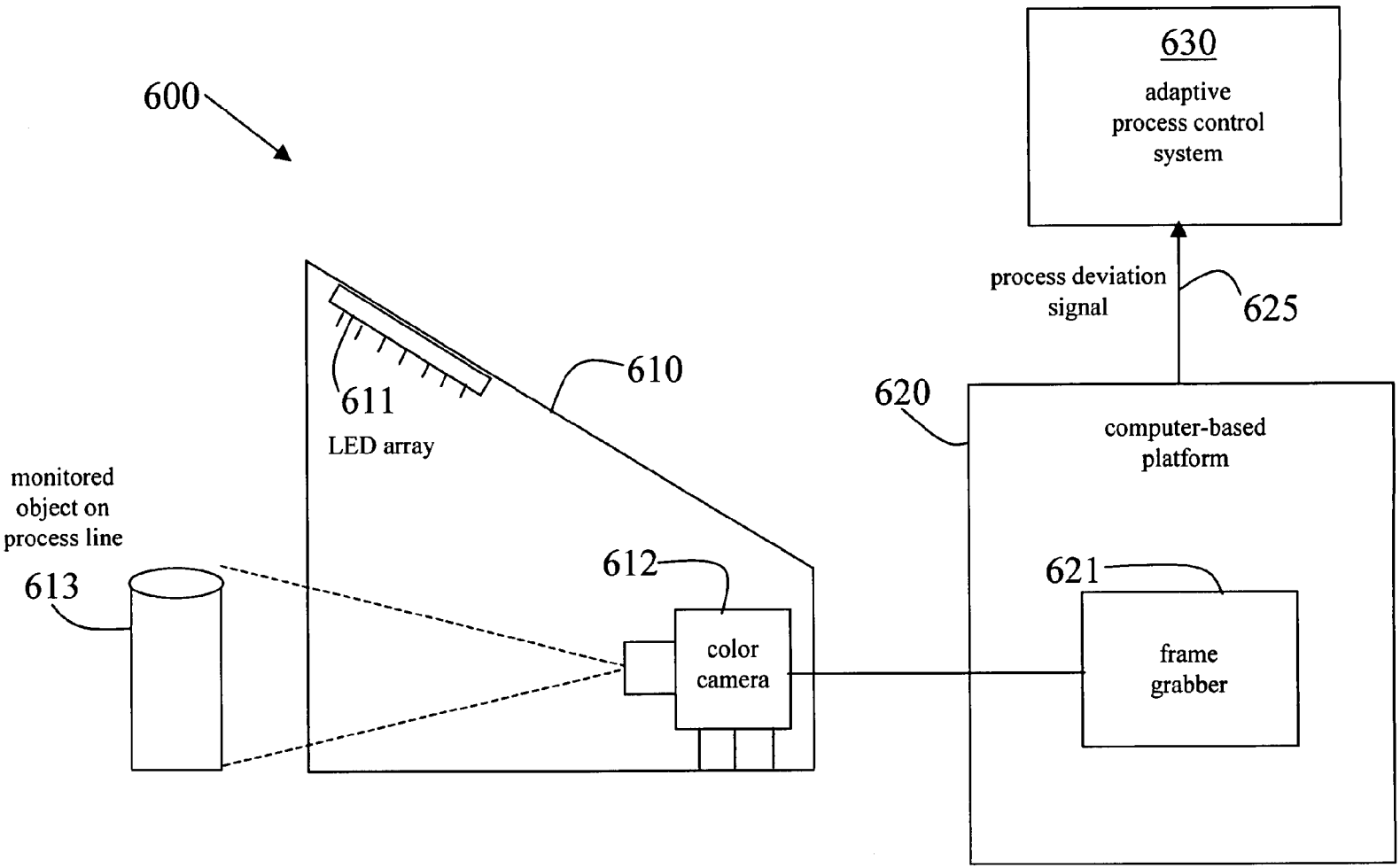
FIG. 6 illustrates an embodiment of a vision monitoring system for monitoring a process, in accordance with various aspects of the present invention.

FIG. 6 illustrates an embodiment of a vision monitoring system 600 for monitoring a process, in accordance with various aspects of the present invention. The process may be continuously monitored in real-time or periodically, in accordance with various aspects of the present invention. The monitoring system 600 includes an imaging assembly 610 which includes a source of illumination 611 and a color camera 612 to collect images of monitored objects 613 on a process line. The monitoring system 600 also includes a computer-based platform 620 connected to the color camera 612 in order to store and process image data collected by the color camera 612 of the monitored object 613.

In accordance with an embodiment of the present invention, the computer-based platform 620 comprises a standard, commercial, off-the-shelf personal computer (PC) running a general purpose operating system. However, the computer-based platform 620 also includes image processing software tools which may be commercially available and/or customized software. In accordance with an embodiment of the present invention, the computer-based platform 620 also provides control signals to the color camera 612 in order to control certain functionality of the color camera 612 (e.g., focusing).

In accordance with an embodiment of the present invention, the color camera 612 outputs analog imaging signals and the computer-based platform 620 includes a frame grabber 621 to convert the analog imaging signals to frames of digital imaging data. In accordance with another embodiment of the present invention, the color camera 612 outputs digital imaging signals and the frame grabber 621 is not used. The color camera 612 comprises a three-color camera providing RGB (red, green, blue) color imaging signals. In accordance with an alternative embodiment of the present invention, the camera 612 comprises a gray scale or monochrome camera.

The imaging assembly 610 is positioned (i.e., mounted) on a product processing line such that a portion of the objects (e.g., printed soda cans) moving past the imaging assembly 610 on the processing line and facing the color camera 612 may be imaged by the color camera 612 while being illuminated by the source of illumination 611 (e.g., an array of white LEDs). In accordance with an embodiment of the present invention, the imaging assembly 120 of FIG. 1 may be detached from the rotatable staging platform 110 of the training system 100 and used as the imaging assembly 610 in the process monitoring system 600 on a processing line. Alternatively, the imaging assembly 610 may be independent of the imaging assembly 120 used to collect reference images. Similarly, the computer-based platform 130 of FIG. 1 may be used as the computer-based platform 620 in the monitoring system 600 or may be a separate, independent computer-based platform. In either case, the computer-based platform 620 includes stored reference images of at least one reference object as previously described.

If the imaging part of the monitoring system 600 is different than the imaging part of the training system 100, then the methods employed in U.S. patent application Ser. No. 10/404,027, filed on Apr. 1, 2003, which is incorporated herein by reference in its entirety, may be used to convert and transfer the reference images from the training system 100 to the monitoring system 600.

The monitoring system 600 may also include a user interface including a display which may be used by an operator to view images and to control the monitoring system 600 via, for example, a menu-driven touch-screen display. The user interface connects to the computer-based platform 620.

In accordance with an alternative embodiment of the present invention, any given reference image corresponding to a particular spatial orientation (e.g., a precise rotational position on a turn-table with respect to a color camera) comprises a composite reference image which is a composite of a plurality of images, each being from a different reference object but having the same spatial orientation. For example, such a composite reference image could be a simple average of several images from different reference objects.

Figure 7:
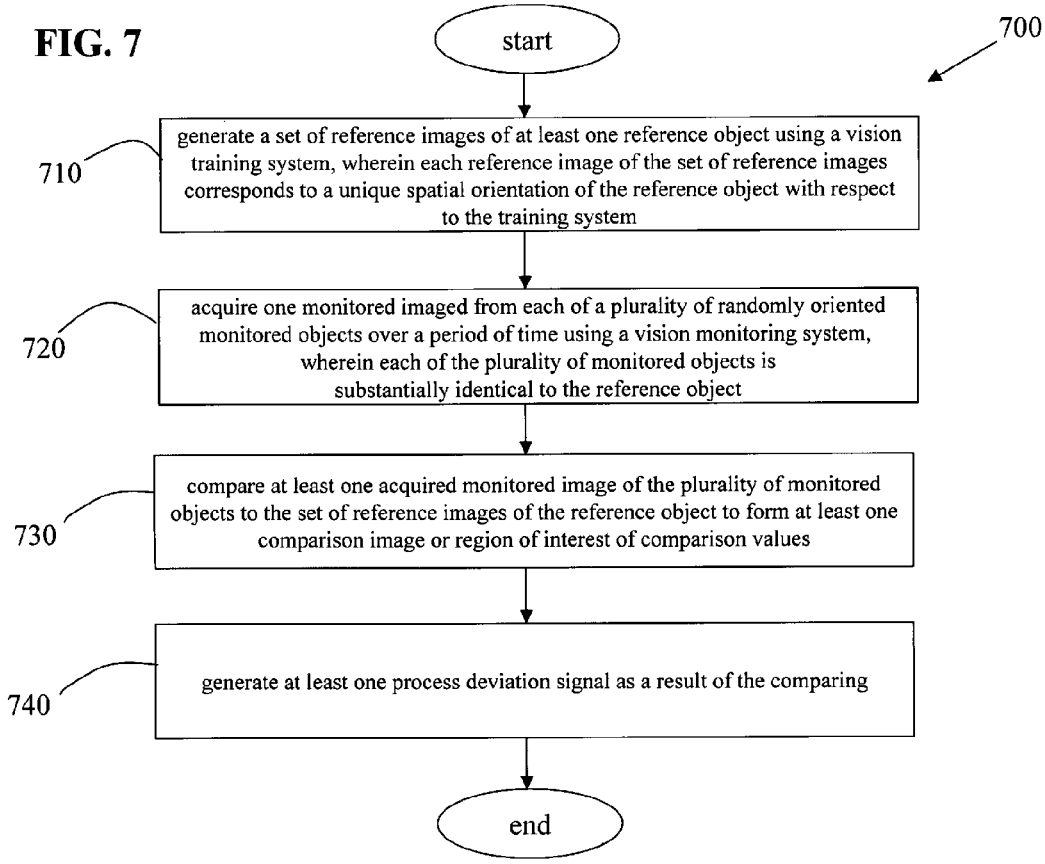
FIG. 7 illustrates a flowchart of an embodiment of a method to generate reference images using the training system of FIG. 1, and to monitor a process using the monitoring system of FIG. 6, in accordance with various aspects of the present invention.

FIG. 7 illustrates a flowchart of an embodiment of a method 700 to generate reference images using the training system 100 of FIG. 1, and to monitor a process using the monitoring system 600 of FIG. 6, in accordance with various aspects of the present invention. In step 710, a set of reference images of at least one reference object is generated using a vision training system, wherein each reference image of the set of reference images corresponds to a unique spatial orientation (e.g., rotational position) of the reference object with respect to the training system. For example, when the reference object is a soda can, sixteen reference images of the soda can are generated at sixteen precise rotational positions. In step 720, one monitored image is acquired from each of a plurality of randomly oriented monitored objects over a period of time (e.g., objects moving on a process line) using a vision monitoring system, wherein each of the plurality of monitored objects is substantially identical to the reference object (e.g., substantially the same colors, same patterns, same positioning of text). In step 730, at least one acquired monitored image of the plurality of monitored objects is compared to the set of reference images of the reference object to form at least one comparison image or region-of-interest of comparison values. In step 740, at least one process deviation signal is generated as a result of the comparing. Steps 730 and 740 are performed by, for example, the computer-based platform 620.

Figure 8:
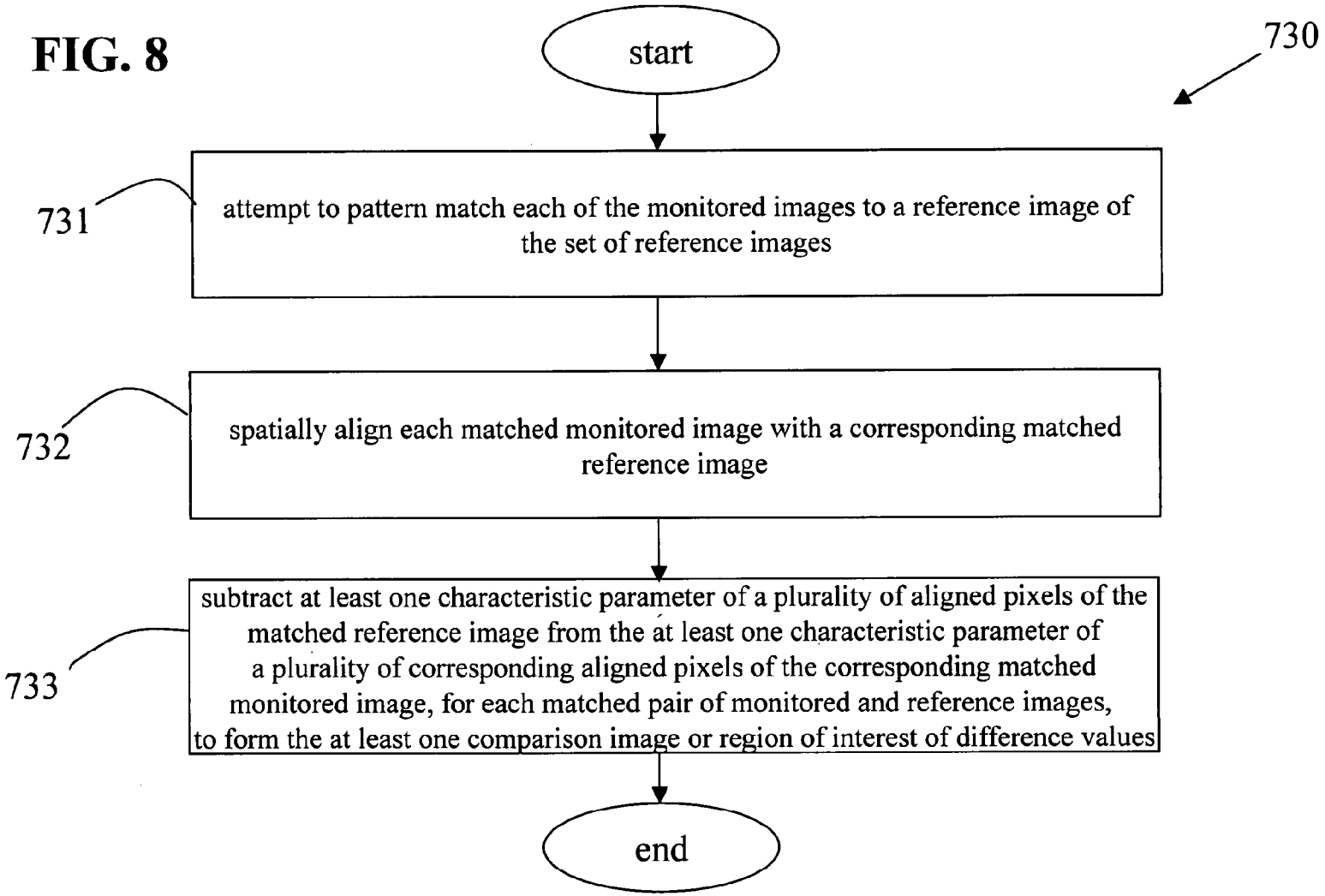
FIG. 8 illustrates a flowchart of an embodiment of a comparison step performed in the method of FIG. 7, in accordance with various aspects of the present invention.

FIG. 8 illustrates a flowchart of an embodiment of the comparison step 730 performed in the method 700 of FIG. 7, in accordance with various aspects of the present invention. In step 731, an attempt is made to pattern match each of the monitored images to a reference image of the set of reference images. All of the reference images are tried, one at a time, to determine a best match to a monitored image. A confidence measure is generated for each reference image to determine which reference image provides the best match to the monitored image. If the resultant confidence measure for each reference image is below a certain predetermined value, then no match is accomplished and the monitored image is not used further in the monitoring process. In step 732, each matched monitored image is spatially aligned with a corresponding matched reference image. In step 733, a characteristic parameter (e.g., a RGB color value) of each aligned pixel of the matched reference image is subtracted from a characteristic parameter of each corresponding aligned pixel of the corresponding matched monitored image to form the at least one comparison image of difference values. The subtraction is performed for each matched pair of monitored and reference images. In step 740, the process deviation signal is generated from the comparison image of difference values (see FIG. 7).

In accordance with an alternative embodiment of the present invention, only a subset of pixels corresponding to a region-of-interest (ROI) of the matched images may be compared, thus reducing the amount of computational operations required to complete the comparison, or simply to focus on a part of the object requiring more sensitive inspection. The ROI may comprise, for example, a disk-shape area, a square area, a rectangular area, or some other shaped area.

During monitoring, about $1/8^{th}$ of the soda can is acquired as an image to increase the probability of determining a match since each reference image corresponds to $1/16^{th}$ of the soda can, in accordance with an embodiment of the present invention.

The characteristic parameter may comprise, for example, RGB color data for qualitative comparisons (e.g., looking for printing flaws on a soda can), or absolute colorimetric data such as XYZ color data or L*a*b* color data for true color comparisons. As a result, the comparison image of difference values may comprise, for example, ΔRΔGΔB values, ΔXΔYΔZ colorimetric values, ΔL*Δa*Δb* colorimetric values, or ΔE colorimetric values. Typically, for qualitative colorimetric comparisons, only selected regions-of-interest (ROI) of the images are compared to cut down on the amount of processing.

As an example, the pixel data may comprise RGB values from the three-color camera 612. These RGB values may be used directly to form the comparison image by subtracting the RGB pixel values of the matched reference image from the RGB pixel values of the matched monitored image. In this way, qualitative differences can be ascertained from the comparison image.

For colorimetric comparisons, RGB pixel values (corrected for lighting variations) are averaged and converted to XYZ or L*a*b* colorimetric values for a predetermined ROI of the matched pair of reference and monitored images. Multiple RGB pixels are averaged and then the colorimetric values are generated using a color transformation algorithm. The averaging helps reduce noise that is present in the original RGB data. As a result, a single colorimetric value is determined for the ROI of the reference image and a single colorimetric value is determined for the corresponding aligned ROI of the monitored image.

Next, the single colorimetric value for the predetermined region-of-interest (ROI) of the matched reference image is subtracted from the single colorimetric value for the corresponding aligned ROI of the matched monitored image, forming a ΔXΔYΔZ or ΔL*Δa*Δb* colorimetric difference value. This difference value is used for quantitative comparisons of absolute color in the ROI. As an alternative, the entire matched images can be averaged, converted to colorimetric values, and subtracted, instead of just the ROI. However, this requires more processing.

Figure 9:
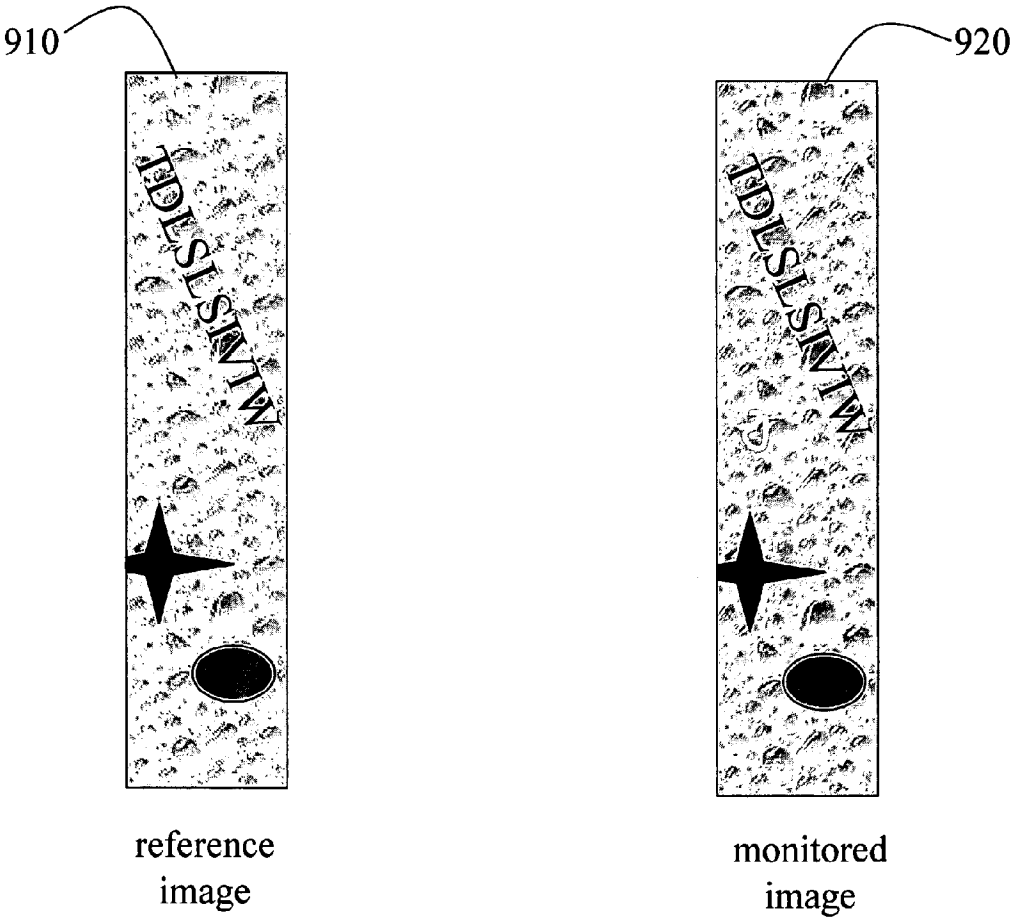
FIG. 9 illustrates an exemplary reference image which is to be compared to an exemplary monitored image, in accordance with the method of FIG. 7.

As an example, FIG. 9 illustrates an exemplary reference image 910 which is to be compared to an exemplary monitored image 920, in accordance with the method 700 of FIG. 7 and FIG. 8. The reference image 910 and the monitored image 920 are a matched pair of aligned color images which are a result of steps 710-732 of the method 700. The matched pair of images 910 and 920 correspond to a vertical section of the printed outside surface of a common, largely cylindrical soda can. The pixels making up the two images 910 and 920 are represented as RGB data (i.e., the characteristic parameter is RGB color data).

Figure 10:
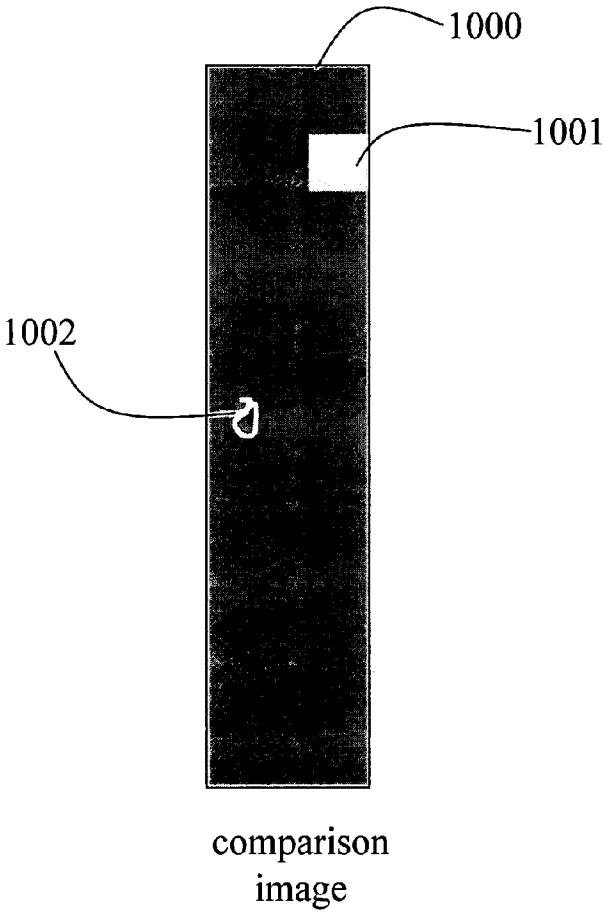
FIG. 10 illustrates an exemplary comparison image generated by subtracting the reference image of FIG. 9 from the monitored image of FIG. 9, in accordance with the method of FIG. 7.

FIG. 10 illustrates an exemplary comparison image 1000 generated by subtracting the reference image 910 of FIG. 9 from the monitored image 920 of FIG. 9 on a pixel-by-pixel basis, in accordance with the method 700 of FIG. 7 and FIG. 8. The comparison. image 1000 is a result of step 733 of the method 700. In step 733, the pixel values of the resultant comparison image 1000 are ΔRΔGΔB data values. The comparison image 1000 indicates any difference between the ideal reference image 910 and the monitored image 920. A subtle difference in RGB color (i.e., ΔRΔGΔB data values) 1001 is seen in the comparison image 1000 which may be due to a deviation in one of the colors of ink used to print the soda can. Also, a not so subtle difference 1002 is seen which may be due to, for example, a scratch or flaw being introduced on the surface of the soda can after printing by some part of the process line.

In step 740, at least one process deviation signal is generated from the comparison image data. For example, the values ΔRΔGΔB of the comparison image 1000 of FIG. 10 are converted to ΔE (Euclidean distance) values for each pixel of the comparison image as $$\Delta E = \sqrt{(\Delta R)^2 + (\Delta G)^2 + (\Delta B)^2}$$

Each ΔE value for each pixel is compared to a predetermined threshold. A count value is generated corresponding to the number of comparison image pixels whose ΔE values are greater than (or, alternatively, less than) the predetermined threshold. This count value is output as the process deviation signal 625 (see FIG. 6) by the computer based platform 620 and may indicate a pass or a fail condition when compared to another predetermined pass/fail threshold. The process deviation signal 625 may be used as an input to an adaptive process control system 630 to bring the process back into spec (see FIG. 6).

In accordance with an embodiment of the present invention, the ΔRΔGΔB values are scaled such that comparison image difference values of zero correspond to a value of 128 on a RGB color scale of 0-255. As a result, both positive (greater than 128) and negative (less than 128) ΔRΔGΔB values are accommodated on the 0-255 RGB color scale, which represents 256 distinct color differences.

For quantitative colorimetric evaluation, ΔXΔYΔZ or ΔL*Δa*Δb* colorimetric data can be used to calculate a Euclidean distance for averaged pixels in a region of interest as, for example, $$\Delta E = \sqrt{(\Delta L^*)^2 + (\Delta a^*)^2 + (\Delta b^*)^2}$$

The pixels in a ROI are averaged, forming an average characteristic parameter value (e.g., average RGB color value), and converted to a L*a*b* colorimetric value, for example. This is done for both the reference image and the corresponding aligned monitored image. The difference is taken and constitutes a process deviation signal or value (e.g., ΔL*Δa*Δb* value) which can be used as an input to an adaptive process control system 630 to adjust color.

As a matter of practicality, not every soda can passing by the monitoring system 600 on the process line may be properly imaged (i.e., some images may be of poor quality and need to be discarded) or matched to a reference image (e.g., when the confidence measure is low). In such a process monitoring situation, it is not important to check and characterize every monitored object (e.g., every soda can). Instead, it is important to obtain a good sampling of the soda cans as they go by such that the process deviation signal 625 is monitored over time to make sure the process (e.g., color printing process of the soda cans) is not getting out of control. For example, in accordance with an embodiment of the present invention, the process deviation signal 625 may be a running average of the count value described above. Other process deviation value signals are possible as well, in accordance with various embodiments of the present invention.

Figure 11:
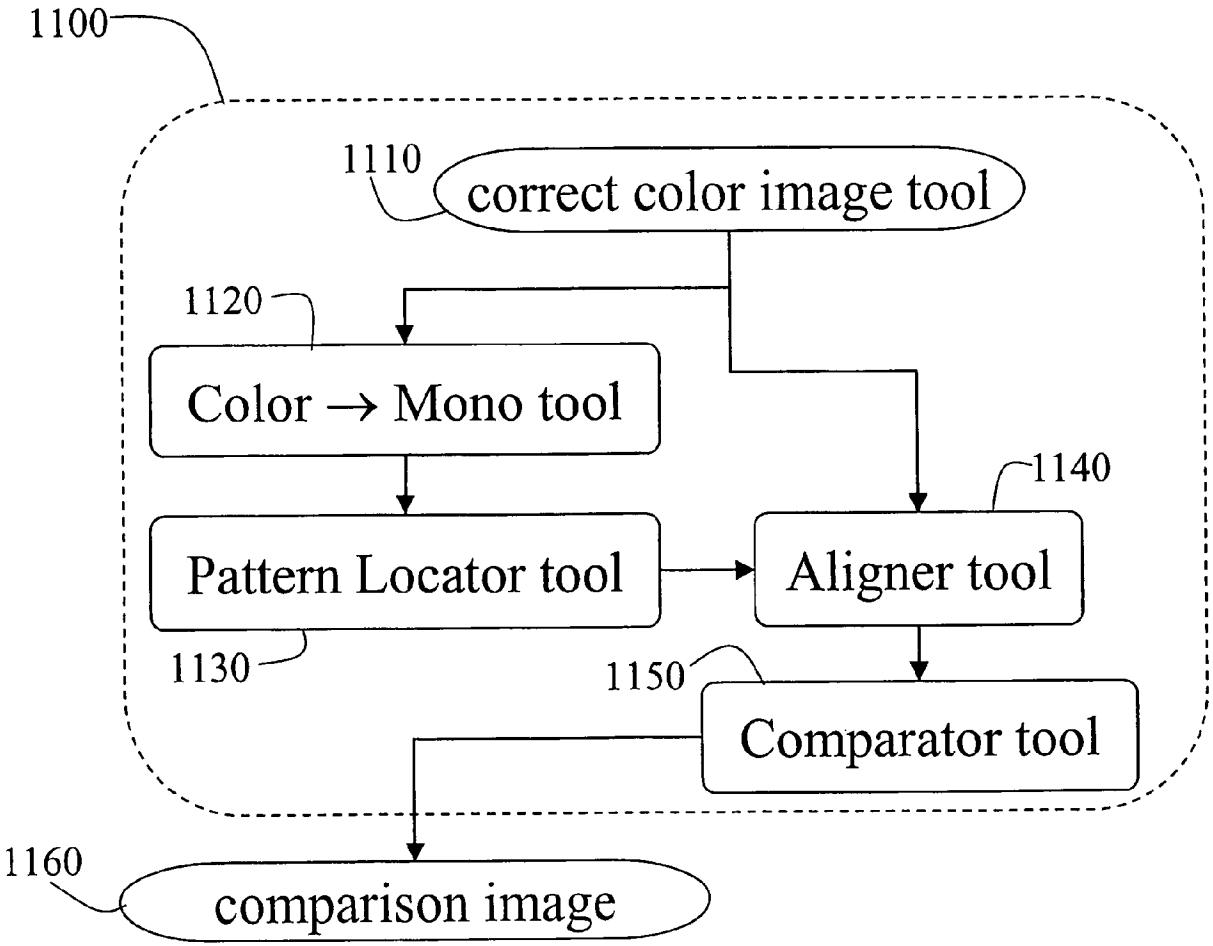
FIG. 11 illustrates a schematic block diagram of a set of software tools used by a computer-based platform of the monitoring system of FIG. 6 to process image information, in accordance with an embodiment of the present invention.

FIG. 11 illustrates a schematic block diagram of a set of software tools 1100 used by a computer-based platform 620 of the monitoring system 600 of FIG. 6 to process image information, in accordance with an embodiment of the present invention. The set of software tools 1100 includes a correct color image tool 1110, a color-to-mono tool 1120, a pattern locator tool 1130, an aligner tool 1140, and a comparator tool 1150. The output of the comparator tool is the comparison image 1160. These tools may include commercial, off-the-shelf tools and/or customized tools in accordance with various embodiments of the present invention.

When reference images are captured by the training system 100, the reference images are corrected for lighting non-uniformity by the correct color image tool 1110. Similarly, when monitored images are captured by the monitoring system 600, the monitored images are corrected for lighting non-uniformity by the correct color image tool 1110. As a pre-processing step to pattern location, the reference images and a monitored image to be compared may be converted from color to monochrome (e.g., to a gray scale pattern or a simple edge pattern), using the color-to-mono tool 1120 to make the pattern locator process simpler.

Figure 12:
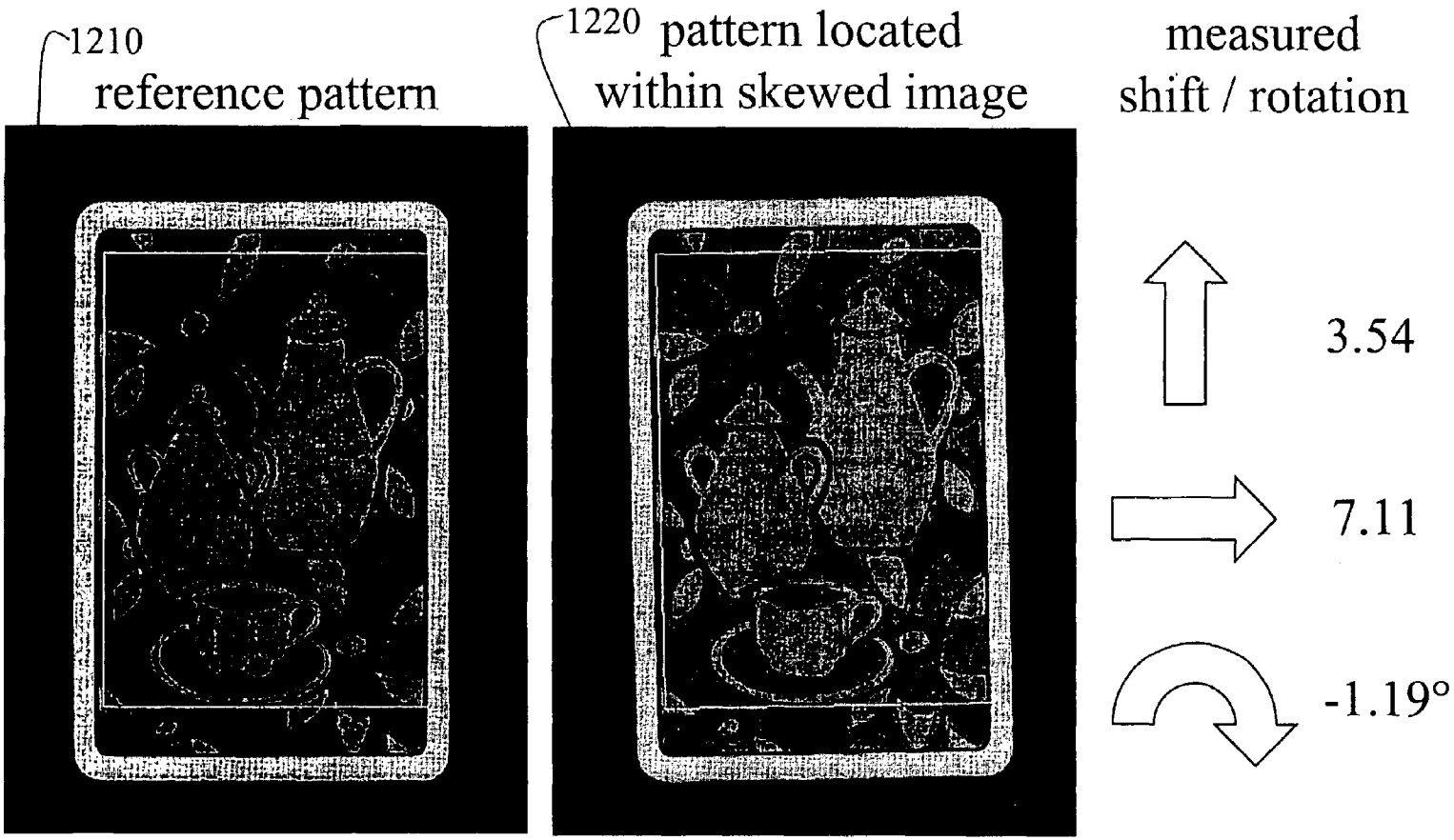
FIG. 12 illustrates the concept of pattern matching performed by the pattern locator tool of FIG. 11 as part of the method step of FIG. 8, in accordance with an embodiment of the present invention.

The pattern locator tool 1130 takes the monitored image and tries to match its pattern to that of one of the reference images. FIG. 12 illustrates the concept of pattern matching performed by the pattern locator tool 1130 of FIG. 11 as part of the method step 731 of FIG. 8, in accordance with an embodiment of the present invention. A monitored image 1220 is compared to a reference image 1210 and a pattern match is achieved. However, the matched pattern of the monitored image 1220 is spatially skewed with respect to the reference image 1210. For example, the matched pattern of the monitored image 1220 is 3.54 pixels too high, 7.11 pixels too far to the right, and rotated −1.19 degrees with respect to a pixel coordinate system of the reference image 1210.

Figure 13:
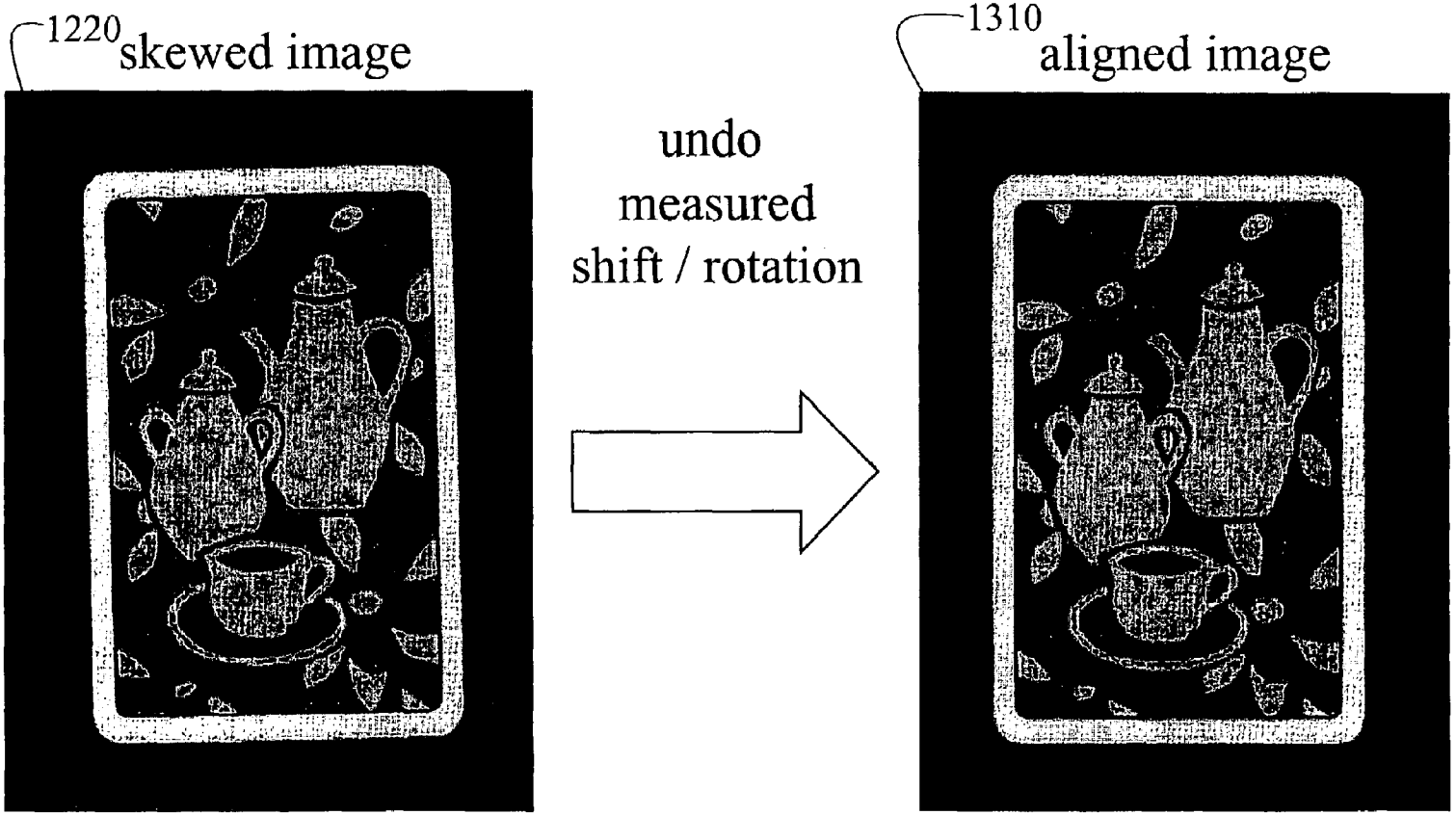
FIG. 13 illustrates the concept of spatial alignment performed by the aligner tool of FIG. 11 as part of the method step of FIG. 8, in accordance with an embodiment of the present invention.

The aligner tool 1140 is used to align the monitored image 1220 to the reference image 1210 based on the skew parameters (3.54, 7.11, −1.19°) calculated as part of the pattern matching process. FIG. 13 illustrates the concept of spatial alignment performed by the aligner tool 1140 of FIG. 11 as part of the method step 732 of FIG. 8, in accordance with an embodiment of the present invention. The skewed monitored image 1220 is transformed to an aligned image 1310 (i.e., undoing the measured shift and rotation) by the aligner tool 1140. The alignment operation is performed on the color monitored image (not the corresponding monochrome image used for pattern matching).

Whether doing qualitative comparisons on RGB data or quantitative comparisons on colorimetric data, an aligned image is used for comparison to the reference image or a region of interest of the reference image.

Figure 14:
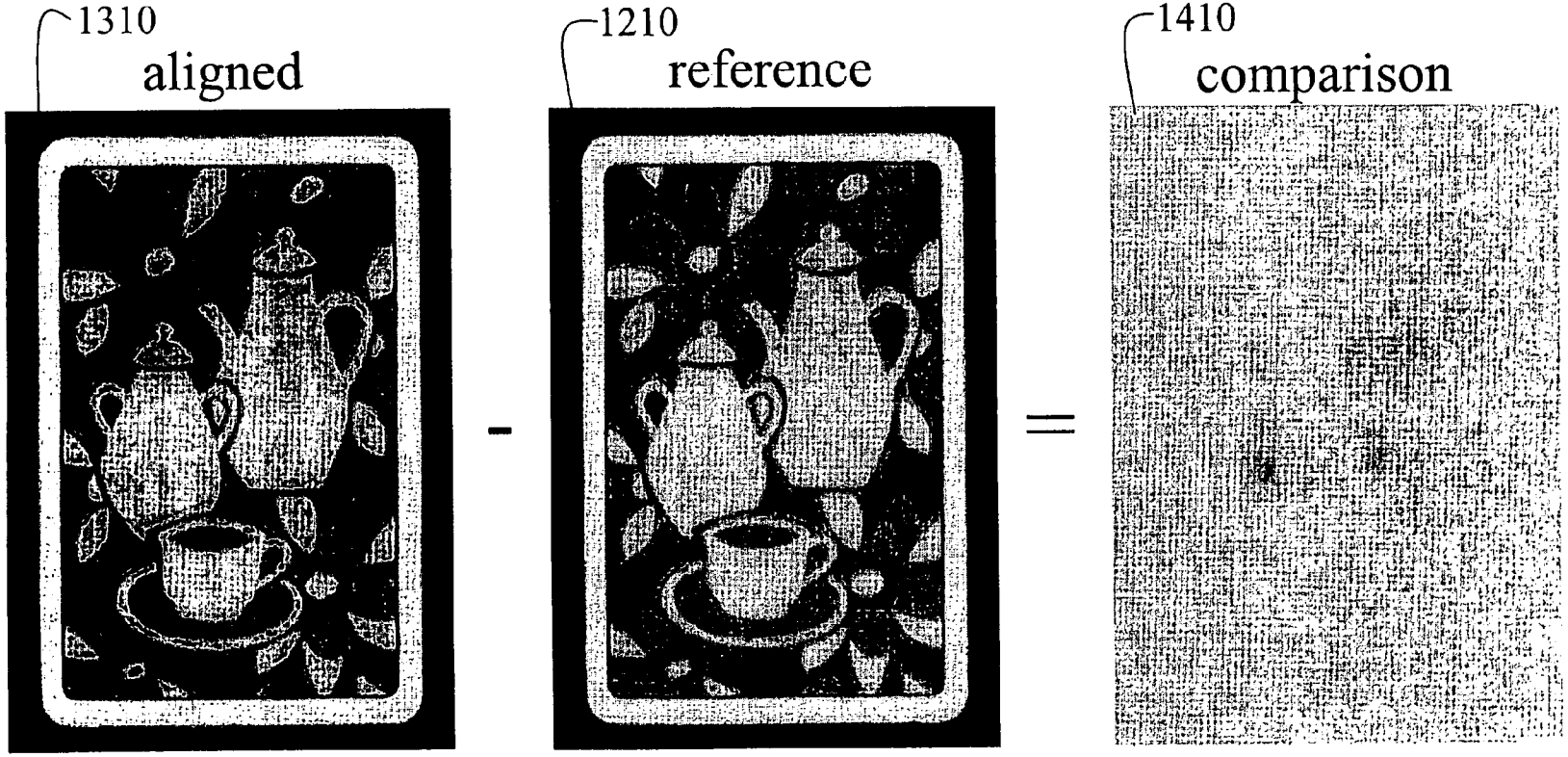
FIG. 14 illustrates the concept of generating a comparison image using the comparator tool of FIG. 11 as part of the method step of FIG. 8, in accordance with an embodiment of the present invention.

FIG. 14 illustrates the concept of generating a comparison image 1160 using the comparator tool 1150 of FIG. 11 as part of the method step 733 of FIG. 8, in accordance with an embodiment of the present invention. A comparison image 1410 of pixels is formed in step 733 of the method 700 by, for example, performing a simple subtraction of the RGB values of corresponding pixels to obtain a comparison image 1410 of ΔRΔGΔB values.

Alternatively, a comparison image 1410 of pixels is formed in step 733 of the method 700 by, for example, first converting the RGB pixel values of the matched pair of images to XYZ or L*a*b* colorimetric data using a color transformation algorithm. The resultant comparison image comprises ΔXΔYΔZ or ΔL*Δa*Δb* colorimetric data as previously described.

Also, a ROI of RGB data can be averaged for the reference image and the matched monitored image, converted to colorimetric data, and then subtracted to form a colorimetric difference value (i.e., a process deviation signal).

In practical applications, both a ΔRΔGΔB comparison image and a ΔXΔYΔZ or ΔL*Δa*Δb* comparison value, based on a region of interest (ROI), are generated. The ΔRΔGΔB comparison image is used for a qualitative assessment of the process and the ΔXΔYΔZ or ΔL*Δa*Δb* comparison value is used for quantitative assessment of color.

As described before, a process deviation signal 625 may be generated using thresholding and counting techniques, or other techniques as well, in accordance with various embodiments of the present invention. Again, the process deviation signal 625 may be used as an input to an adaptive process control system 630 to bring the process back into control. Alternatively, the process deviation signal may be used by an operator to manually adjust the process.

In summary, a method and system to monitor randomly oriented objects on a production process line are disclosed. A color camera is used initially to collect a set of reference images of at least one reference object. The reference images represent various spatial orientations of the reference object. The reference object serves as the standard for the process. The reference images are stored in a computer-based platform. The color camera is then used to capture images of monitored objects as the monitored objects pass by the color camera on a process line. The monitored objects may have a random spatial orientation with respect to the color camera as the monitored objects pass through the field-of-view of the color camera. The captured images of the monitored objects are processed by the computer-based platform and compared to the reference images in order to determine if certain characteristic parameters of the monitored objects have deviated from those same characteristic parameters of the reference object. If so, the process may be adjusted to correct for the deviations in order to bring the process back into tolerance.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for monitoring a process, said method comprising:

generating a set of reference images of at least one reference object using a vision training system, wherein each reference image of said set of reference images corresponds to a unique spatial orientation of said reference object with respect to said training system;

acquiring one monitored image from each of a plurality of randomly oriented monitored objects over a period of time using a separate vision monitoring system, wherein each of said plurality of monitored objects is substantially identical to said reference object;

comparing at least one acquired monitored image of said plurality of monitored objects to said set of reference images of said reference object to form at least one comparison image of comparison values or region of interest of comparison values; and generating at least one process deviation signal in response to said comparing.

2. The method of claim 1 wherein said comparing comprises:

attempting to pattern match each of said monitored images to a reference image of said set of reference images;

spatially aligning each matched monitored image with a corresponding matched reference image; and subtracting at least one characteristic parameter of a plurality of aligned pixels of said matched reference image from at least one characteristic parameter of a plurality of corresponding aligned pixels of said corresponding matched monitored image, for each matched pair of monitored and reference images, to form said at least one comparison image or region of interest of difference values.

3. The method of claim 2 further comprising calculating said at least one characteristic parameter for said plurality of aligned pixels of said matched monitored image and said corresponding matched reference image, for each matched pair of monitored and reference images, before performing said subtraction.

4. The method of claim 2 wherein said at least one characteristic parameter comprises RGB color data.

5. The method of claim 3 wherein said at least one characteristic parameter comprises colorimetric data.

6. The method of claim 1 wherein said at least one process deviation signal comprises a pass/fail value.

7. The method of claim 1 wherein said at least one process deviation signal comprises colorimetric data.

8. The method of claim 1 further comprising feeding back said at least one process deviation signal to a process control system to correct for a deviation in said process.

9. The method of claim 1 wherein said generating said at least one process deviation signal comprises counting every pixel in said at least one comparison image or said region of interest having a comparison value greater than or less than a first predetermined threshold value.

10. The method of claim 1 further comprising correcting said set of reference images and each of said monitored images for non-uniform lighting before said comparing step.

11. A vision training system for characterizing a reference object, said training system comprising:

a rotatable staging platform to stage a reference object;

a source of illumination to illuminate said reference object on said staging platform;

a color camera to collect a set of reference images of said reference object as said reference object rotates on said rotatable staging platform, wherein each reference image of said set of reference images corresponds to a unique rotatable position of said reference object with respect to said color camera; and a computer-based platform connected to said color camera to store and process said set of reference images.

12. The training system of claim 11 wherein said rotatable staging platform comprises a turntable.

13. The training system of claim 11 wherein said source of illumination comprises an array of light emitting diodes which emits a spectrum of white light.

14. The training system of claim 11 wherein said computer-based platform includes a frame grabber to convert analog signals, output from said color camera, to digital signals representing single frames of digital imaging data.

15. The training system of claim 11 wherein said color camera outputs analog imaging signals.

16. The training system of claim 11 wherein said color camera outputs digital imaging signals.

17. The training system of claim 11 wherein said rotatable staging platform is detachable from said training system, leaving a monitoring system comprising said source of illumination, said color camera, and said computer-based platform, said monitoring system being mountable on a process line to image objects to be monitored.

18. A vision monitoring system for monitoring a process, said monitoring system comprising:

a source of illumination positioned to illuminate objects to be monitored as said objects move along a process line in spatially random orientations;

a color camera positioned on said process line to capture at least one image from each illuminated object, forming a plurality of monitored images, as each illuminated object passes through a field-of-view of said color camera; and a computer-based platform storing a set of reference images and being connected to said color camera to store said plurality of monitored images and to generate at least one process deviation signal by comparing at least one monitored image of said plurality of monitored images to said set of reference images, wherein said set of reference images correspond to unique rotational positions of at least one reference object, wherein said objects to be monitored are substantially identical to said at least one reference object.

19. The monitoring system of claim 18 wherein said computer-based platform includes a frame grabber to convert analog signals, output from said color camera, to digital signals representing single frames of digital imaging data.

20. The monitoring system of claim 18 wherein said source of illumination comprises an array of light emitting diodes which emits a spectrum of white light.

21. The monitoring system of claim 18 wherein said color camera outputs analog imaging signals.

22. The monitoring system of claim 18 wherein said color camera outputs digital imaging signals.

23. The monitoring system of claim 18 wherein said at least one process deviation signal comprises at least one of a pass/fail value and colorimetric data.

24. The monitoring system of claim 18 wherein said comparing, performed by said computer-based platform, comprises:

attempting to pattern match each of said plurality of monitored images to at least one reference image of said set of reference images;

spatially aligning each matched monitored image with a corresponding matched reference image; and subtracting at least one characteristic parameter of a plurality of aligned pixels of said matched reference image from said at least one characteristic parameter of a plurality of corresponding aligned pixels of said corresponding matched monitored image, for each matched pair of monitored and reference images, to form at least one comparison image of difference values or region of interest of difference values.

25. The monitoring system of claim 24 wherein said at least one characteristic parameter is calculated for said plurality of aligned pixels of said matched monitored image and said corresponding matched reference image, before said subtracting, for each matched pair of monitored and reference images.

26. The monitoring system of claim 25 wherein said at least one characteristic parameter comprises colorimetric data.

27. The monitoring system of claim 24 wherein said at least one characteristic parameter comprises RGB color data.

28. The monitoring system of claim 24 wherein said at least one process deviation signal is generated by counting every pixel in said at least one comparison image or region of interest having a difference value greater than or less than a first predetermined threshold value.

29. The monitoring system of claim 18 wherein said at least one process deviation signal is used to correct a deviation in said process.

30. A method for monitoring a process, said method comprising:

generating a set of reference images of at least one reference object using a vision training system, wherein each reference image of said set of reference images corresponds to a unique spatial orientation of said reference object with respect to said training system;

acquiring one monitored image from each of a plurality of randomly oriented monitored objects over a period of time using a separate vision monitoring system, wherein each of said plurality of monitored objects is substantially identical to said reference object; and comparing at least one acquired monitored image of said plurality of monitored objects to said set of reference images of said reference object to form at least one process deviation signal.

31. The method of claim 30 wherein said comparing comprises:

attempting to pattern match each of said monitored images to a reference image of said set of reference images;

spatially aligning each matched monitored image with a corresponding matched reference image;

averaging at least one characteristic parameter of a plurality of aligned pixels of said matched reference image to form a first average characteristic parameter value, for each matched pair of monitored and reference images;

averaging said at least one characteristic parameter of said plurality of corresponding aligned pixels of said corresponding matched monitored image to form a second average characteristic parameter value, for each matched pair of monitored and reference images;

calculating a first colorimetric parameter value from said first average characteristic parameter value, for each matched pair of monitored and reference images;

calculating a second colorimetric parameter value from said second average characteristic parameter value, for each matched pair of monitored and reference images; and subtracting said first colorimetric parameter value from said second colorimetric parameter value to form said at least one process deviation signal, for each matched pair of monitored and reference images.

32. The method of claim 31 wherein said at least one characteristic parameter comprises RGB color data.

33. A method for monitoring a process, said method comprising:

acquiring one monitored image from each of a plurality of randomly oriented monitored objects over a period of time using a monitoring system, wherein each of said plurality of monitored objects is substantially identical to a reference object;

comparing at least one acquired monitored image of said plurality of monitored objects to a set of stored reference images of said reference object to form at least one comparison image of comparison values, wherein each reference image of said set of stored reference images corresponds to a unique spatial orientation of said reference object with respect to said monitoring system; and generating at least one process deviation signal in response to said comparing.

34. A method of training a vision system, said method comprising:

positioning a reference object onto a rotatable staging platform *of a vision training system*;

illuminating said reference object on said staging platform using a source of illumination *of said vision training system*;

collecting a set of reference images of said reference object with a color camera *of said vision training system* as said reference object rotates on said rotatable staging platform, wherein each reference image of said set of reference images corresponds to a unique and precise rotatable position of said reference object with respect to said color camera; and processing and storing said set of reference images using a computer-based platform *of said vision training system* which is connected to said color camera.

35. A method for monitoring an industrial can or container process, said method comprising:

generating a set of reference images of at least one reference can using a vision training system, wherein each reference image of said set of reference images corresponds to a unique rotational orientation of said reference can with respect to said training system;

acquiring one monitored image from each of a plurality of randomly rotationally oriented monitored cans on a process line over a period of time using a separate vision monitoring system, wherein each of said plurality of monitored cans is substantially identical to said reference can;

comparing at least one acquired monitored image of said plurality of monitored cans to said set of reference images of said reference can to form at least one comparison image of comparison values or region of interest of comparison values; and generating at least one process deviation signal in response to said comparing.

*36. A vision system for characterizing an object, said system comprising:*

*a rotatable staging platform to stage an object;*

*a source of illumination to illuminate said staged object on said staging platform;*

*a color camera to collect a set of images of said staged object as said staged object rotates on said rotatable staging platform, wherein each image of said set of images corresponds to a unique rotatable position of said staged object with respect to said color camera; and*

*a computer-based platform storing a set of reference images and being connected to said color camera to store and process said set of images of said staged object and to generate at least one process deviation signal by comparing at least one image of said set of images of said staged object to said set of reference images, wherein the set of reference images correspond to unique rotational positions of at least one reference object, and wherein said at least one reference object is substantially identical to said staged object.*

*37. The system of claim 36 wherein said rotatable staging platform comprises a turntable.*

*38. The system of claim 36 wherein said source of illumination comprises an array of light emitting diodes which emits a spectrum of white light.*

*39. The system of claim 36 wherein said computer-based platform includes a frame grabber to convert analog signals, output from said color camera, to digital signals representing single frames of digital imaging data.*

*40. The system of claim 36 wherein said color camera outputs analog imaging signals.*

*41. The system of claim 36 wherein said color camera outputs digital imaging signals.*

* * * * *